(12) United States Patent
Dauben et al.

(10) Patent No.: US 6,291,615 B1
(45) Date of Patent: Sep. 18, 2001

(54) CATALYST SYSTEM, THE USE THEREOF IN THE POLYMERIZATION OF DIENES IN A SOLUTION, SUSPENSION AND VAPOR PHASE AND THE USE OF DIENE RUBBERS PRODUCED THEREWITH

(75) Inventors: Michael Dauben, Neuss; Rüdiger Engehausen, Dormagen, both of (DE); Heinz Hermann Greve, Brights Grove (CA); Wolfgang Nentwig, Bergisch Gladbach (DE); Walter Kaminsky, Pinneberg (DE); Christian Strübel; Volker Scholz, both of Hamburg (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/367,239

(22) PCT Filed: Feb. 10, 1998

(86) PCT No.: PCT/EP98/00739

§ 371 Date: Aug. 10, 1999

§ 102(e) Date: Aug. 10, 1999

(87) PCT Pub. No.: WO98/36004

PCT Pub. Date: Aug. 20, 1998

(30) Foreign Application Priority Data

Feb. 17, 1997 (DE) ............................. 197 06 027
Feb. 17, 1997 (DE) ............................. 197 06 026
Feb. 17, 1997 (DE) ............................. 197 06 025

(51) Int. Cl.$^7$ ............................. C08F 4/16; C08F 4/64; C08F 112/34; C08F 136/06
(52) U.S. Cl. ............................. 526/160; 526/127; 526/943; 526/335; 526/340.4; 502/104; 502/152
(58) Field of Search ............................. 526/160, 161, 526/943, 335, 340.4; 502/104, 152

(56) References Cited

U.S. PATENT DOCUMENTS

| 3,023,203 | 2/1962 | Dye | 260/94.9 |
| 4,874,880 | 10/1989 | Miya et al. | 556/53 |
| 5,858,903 | 1/1999 | Sylvester et al. | 502/153 |
| 5,908,904 | 6/1999 | Sylvester et al. | 526/153 |

FOREIGN PATENT DOCUMENTS

| 4332009 | 3/1995 | (DE) . |
| 97/07141 | 2/1997 | (WO) . |

OTHER PUBLICATIONS

Oliva et al., Polymerization of 1,3–alkadienes in the presence of Ni–and Ti–based catalytic systems containing methylalumoxane, Makromol. Chem., Rapid Communications, 11, 519–524 (1990).*
Porri et al., Influence of monomer structure on chemo–and stereoselectivity fo 1,3–diene polymerization, Macromol. Symp., 89, 383–392 (1995).*
Ullmanns Encyklopadie der technischen Chemie [Ullmann's Encyclopadedia of Chemical Technology], Verlag Chemie Weinheim, 4th edition, vol. 13, pp. 602–604.
Handbuch Fur die Gummi–industrie, (Handbook for the Rubber Industry), Bayer AG, 2nd edition Chapter A8.1 (date unavailable).
L. Oliva, P. Longo, A. Grassi, P. Ammendola, C. Pellecchia, Markromol. Chem. Rapid Commun. 11, pp. 519–524, 1990.
G. Ricci, L. Porri, A. Giarrusso, Macromol Symp. 89 pp. 383–392 (month unavailable) 1995.
Kunststoffe und Elastomer in Kraftfahrzeugen, (Plastics and Elastomers in Motor Vehicles), G. Walter, Verlag W. Kohlhammer Stuttgart, Berlin Cologne,Mainze, (month unavailable) 1985, chapter 4.7.17.
K.H. Nordsiek, Kautschuck, Gummi, Kunststoffe 39 (month unavailable) 1986, pp. 599–611.
R. Bond, G.F. Morton, L.H. Krol, Polymer 25, Jan. 1984, pp. 132–140.

* cited by examiner

*Primary Examiner*—David W. Wu
*Assistant Examiner*—R. Harlan
(74) *Attorney, Agent, or Firm*—Joseph C. Gil; Noland J. Cheung

(57) ABSTRACT

The present invention is directed to a catalyst system, the use thereof in the polymerization of dienes in a solution, suspension and vapor phase, and the use of diene rubbers produced therewith, exhibiting a high cis content, an average vinyl content and a low gel content.

16 Claims, No Drawings

CATALYST SYSTEM, THE USE THEREOF IN THE POLYMERIZATION OF DIENES IN A SOLUTION, SUSPENSION AND VAPOR PHASE AND THE USE OF DIENE RUBBERS PRODUCED THEREWITH

FIELD OF THE INVENTION

The present invention relates to a novel catalyst system, to the use thereof for the solution, suspension and vapour phase polymerization of dienes and to the use of the diene rubbers produced therewith, which have a high cis content, average vinyl content and low gel content.

BACKGROUND OF THE INVENTION

The preparation of polydienes, e.g. cis-polybutadiene (BR), on the basis of metal-organic Ziegler-Natta catalysts is a process which has been used on the industrial scale for a long time. The commercially available grades are characterized by different microstructures. The high-cis grades have cis contents of over 90% and vinyl contents of up to 4%: Nd—BR (97% cis, 2% trans, 1% vinyl), Ni—BR (96% cis, 2% trans, 2% vinyl), Co—BR (95% cis, 3% trans, 2% vinyl), Ti—BR (92% cis, 4% trans, 4% vinyl) (Ullmanns Encyklopädie der technischen Chemie (Ullmann's Encyclopaedia of Chemical Technology), Verlag Chemie, Weinheim, 4th edition, volume 13, pages 602–604; "Handbuch für die Gummi-Industrie" ("Handbook for the Rubber Industry"), Bayer AG, 2nd edition, chapter A8.1).

Li—BR, on the other hand, is prepared by an anionic process using lithium alkyl catalysts. The trans content exceeds the cis content in this case (35% cis, 55% trans, 10% vinyl).

It is further known that high-cis diene rubbers with vinyl contents of >10% can be prepared using metal-organic catalyst systems, especially metallocenes, e.g. cyclopentadienyltitanium trichloride ($CpTiCl_3$)/methylaluminoxane (MAO) (L. Oliva, P. Longo, A. Grassi, P. Ammendola, C. Pellecchia, MaKromol. Chem., Rapid Commun. 11 (1990) 519–524) or cyclopentadienyltributoxytitanium/MAO (G. Ricci, L. Porri, A. Giarrusso, Macromol. Symp. 89 (1995) 383–392).

It is also known to polymerize conjugated dienes in the liquid monomers without the addition of solvents. However, such a process has the disadvantage that complete polymerization is accompanied by the evolution of a large quantity of heat, which is difficult to regulate and is therefore potentially hazardous. Moreover, this process also causes environmental pollution when the polymers are separated from the monomers.

In recent years the vapour phase process has proved particularly advantageous especially for the preparation of polyethylenes and polypropylenes and has achieved industrial success. The environmentally relevant advantages of the vapour phase process are based especially on the fact that no solvents are used and emissions and effluent pollution can be reduced.

EP 647 657 discloses a catalyst system which polymerizes butadiene to very high-cis polybutadiene in the vapour phase. It is further known that a system consisting of $CpTiCl_3$ and MAO is capable of polymerizing butadiene without a solvent (WO 96/04322).

The main areas of application for polybutadiene are tyre manufacture, industrial rubber goods and the modification of plastics.

In tyre manufacture, it is known that the various components, such as tread, side wall, steel belt plies, carcass and heel, are made into the blank and then vulcanized. A high cis content therefore has a positive effect in tyre manufacture because of the compounding adhesiveness and unvulcanized strength ("Kunststoffe und Elastomere in Kraftfahrzeugen" ("Plastics and Elastomers in Motor Vehicles"), G. Walter, Verlag W. Kohlhammer Stuttgart, Berlin, Cologne, Mainz, 1985, chapter 4.7.17; "Handbuch für die Gummi-Industrie" ("Handbook for the Rubber Industry"), Bayer A G, 2nd edition, chapter A8.1).

On the other hand it is known that increasing the vinyl content improves certain properties of the tyre, especially the wet grip. Improving the wet grip ensures greater safety on the road.

For conventional tread compounds, however, an improvement in wet grip is accompanied by a decrease in rolling resistance and hence an increase in motor vehicle fuel consumption and emissions. It has been found that the rolling resistance can be correlated well with the loss factor tan δ recorded at a frequency of 10 Hz and a temperature of 60° C., a drop in the loss factor at 60° C. being accompanied by a decrease in rolling resistance (K. H. Nordsiek, Kautschuk, Gummi, Kunststoffe 39 (1986) 599–611; R. Bond, G. F. Morton, L. H. Krol, Polymer 25 (1984) 132–140).

It is known that tyre properties can be adjusted by compounding various types of synthetic rubber. However, this process is expensive and the problem of phase separation can arise during compounding.

SUMMARY OF THE INVENTION

The object consists in providing a novel catalyst system for the production, in solution, suspension and vapour phase processes, of diene rubbers with a high cis content, average vinyl content and low gel content which have a lower loss factor tan δ at 60° C. (rolling resistance) in rubber compounds, said catalyst system not possessing the disadvantages of the state of the art.

Surprisingly it has now been found that diene rubbers can be produced in high space-time yields by using a fluorine-containing metal-organic compound together with a co-catalyst, and that diene rubbers with low gel contents can be produced in high space-time yields by heterogenizing a fluorine-containing metal-organic compound together with a co-catalyst on an inorganic support and using it in vapour phase polymerization.

Furthermore it has now been found that diene rubbers which have a high cis content and average vinyl content and have a lower loss factor tan δ at 60° C. as well as high elasticity in rubber compounds, and which are thus outstandingly suitable as raw materials in the tyre sector for use in treads and side walls, can be produced in high space-time yields by means of metal-organic catalysts in a one-stage process.

DETAILED DESCRIPTION OF THE INVENTION

Said object is achieved according to the invention by the use of novel, highly active metal-organic catalysts of formula 1:

$$R_nMX_m \qquad (1),$$

wherein M is a metal, the radicals R are identical or different, can be in a bridged or unbridged form and are a mononuclear or polynuclear hydrocarbon radical coordinated with the central atom M, the radicals X are identical or different and are a fluorine, chlorine, bromine or iodine, a hydrogen radical, $C_1$- to $C_{10}$-alkyl, $C_6$- to $C_{15}$-aryl, OR' or OC(O)R', R' being $C_1$- to $C_{10}$-alkyl, $C_6$- to $C_{15}$-aryl, alkylaryl, fluoride, fluoroalkyl or fluoroaryl each having 1 to 10 C atoms in the alkyl moiety and 6 to 20 C atoms in the aryl moiety, and n and m each denote the numbers 0, 1, 2, 3 or 4, where n+m<5.

M is preferably titanium, zirconium, hafnium, vanadium, niobium, tantalum, scandium, yttrium or a rare earth metal, particularly preferably titanium.

X is preferably fluorine or a mixture of fluorine and chlorine, bromine or iodine.

n is preferably 1 or 2, m is preferably 3, 2 or 1 and m+n is preferably 3 or 4.

n is particularly preferably 1, m is particularly preferably 3 and m+n is particularly preferably 4.

R is preferably a substituted or unsubstituted cyclopentadienyl group $(R'')_kCp$, R'' being a hydrogen radical, $C_1$- to $C_{10}$-alkyl, $C_6$- to $C_{15}$-aryl, arylalkyl, alkenyl, fluoroalkyl or fluoroaryl and k is 1–5.

Examples of substituted cyclopentadienyl groups are methylcyclopentadienyl, dimethylcyclopentadienyl, trimethylcyclopentadienyl, pentamethylcyclopentadienyl, ethylcyclopentadienyl, diethylcyclopentadienyl, triethylcyclopentadienyl, tetraethyl-cyclopentadienyl, pentaethylcyclopentadienyl, propylcyclopentadienyl, phenylcyclopentadienyl, ethyltetramethylcyclopentadienyl, propyltetramethylcyclopentadienyl, butyltetramethylcyclopentadienyl, silylcyclopentadienyl, indenyl, methylindenyl, dimethylindenyl, benzindenyl, methylbenzindenyl, dimethylbenzindenyl and trimethylbenzindenyl.

Examples of particularly preferred compounds of formula 1 are:

$CpTiF_3$ $MeCpTiF_3$ $Me_5CpTiF_3$ $(Me_5Cp)_2TiF$ $IndTiF_3$ $IndTiClF_2$ $IndTiCl_2F$ $MeIndTiF_3$ $MeIndTiClF_2$ $MeIndTiCl_2F$ $Me_2IndTiF_3$ $BenzindTiF_3$ $MeBenzindTiF_3$ Co-catalysts which can be used in the process according to the invention are alkylaluminoxanes, butyl-modified aluminoxanes, aluminium alkyls, fluorine-substituted triarylboranes or mixtures of the components. Methylaluminoxane and butyl-modified methylaluminoxane (so-called co-methylaluminoxane) are preferred.

Dienes which can be used in the process according to the invention are butadiene, isoprene, pentadiene and 2,3-dimethylbutadiene, especially butadiene and isoprene. Said dienes can be used either individually or in a mixture with one another to form either homopolymers or copolymers of said dienes.

The polymerization according to the invention is preferably carried out in the presence of inert organic solvents. Examples of suitable inert organic solvents are aromatic, aliphatic and/or cycloaliphatic hydrocarbons such as, preferably, benzene, toluene, hexane, pentane, heptane and/or cyclohexane. The polymerization is preferably carried out in solution or in suspension.

In another preferred embodiment the process according to the invention is carried out in the vapour phase. The polymerization of olefins in the vapour phase was first carried out technologically in 1962 (U.S. Pat. No. 3,023,203). Corresponding fluidized bed reactors have been state of the art for a long time.

The metal-organic compound of formula 1 and the co-catalyst are preferably applied to an inorganic support and used in heterogeneous form. Particularly suitable inert inorganic solids are silica gels, clays, aluminosilicates, talcum, zeolites, carbon black, inorganic oxides such as silicon dioxide, aluminium oxide, magnesium oxide and titanium dioxide, and silicon carbide, preferably silica gels, zeolites and carbon black. Said inert inorganic solids can be used individually or in a mixture with one another. In another preferred embodiment organic supports are used individually or in a mixture with one another or with inorganic supports. Examples of organic supports are porous polystyrene, porous polypropylene or porous polyethylene.

The polymerization according to the invention can be carried out in a temperature range from –90° C. to 180° C., preferably in a temperature range from 50° C. to 150° C.

The present invention further relates to the use of the diene rubbers produced according to the invention, preferably for the manufacture of tyres.

The vinyl content of the diene rubbers is preferably in a range from 5 to 50%, particularly preferably in a range from 10 to 30%. The cis content of the diene rubbers produced according to the invention is preferably over 50%, particularly preferably over 70%, the aim being to minimize the gel contents in all cases.

By virtue of their high cis content coupled with an increased vinyl content, the diene rubbers according to the invention, for example polybutadiene or polyisoprene, produced in a one-stage process by means of metal-organic catalysts, serve as valuable raw materials for the rubber industry and for the modification of plastics. For use in the tyre sector in particular, there are major advantages in respect of rolling resistance by virtue of the low values of the loss factor tan δ at 60° C. as well as elasticity in the tread and side wall.

EXAMPLES

In Examples 1 to 12 below, the polymerizations were carried out batchwise in a glass autoclave. All operations were performed under inert gas.

Example 1

The reactor was thoroughly heated, flushed several times with inert gas, thermo-statted and then charged with 99 ml of toluene, 10 g of butadiene and 0.58 g of methylaluminoxane. A solution of $CpTiF_3$ in toluene ($1 \times 10^{-4}$ mol/l) was injected into the reactor through a septum by means of a gastight syringe and the polymerization was started at a temperature of 30° C.

After a polymerization time of 30 minutes, the butadiene was discharged and the mixture was quenched with ethanol. Precipitation was induced by adding the toluene solution dropwise to ethanol containing Vulkanox KB as stabilizer, and the precipitate was filtered off and dried. The activity was 54 kg BR/mol Ti.h.$C_{butadiene}$. Analysis of the microstructure showed 74% of 1,4-cis, 23% of 1,2-vinyl and 3% of 1,4-trans.

Example 2

The procedure of Example 1 was followed except that the CpTiF$_3$ was replaced with MeCpTiF$_3$. The activity was 80 kg BR/mol Ti.h.C$_{butadiene}$. Analysis of the micro-structure showed 78% of 1,4-cis, 21% of 1,2-vinyl and 1% of 1,4-trans.

Example 3

The procedure of Example 1 was followed except that the CpTiF$_3$ was replaced with Cp*TiF$_3$ (5×10$^{-4}$ mol/l). The activity was 40 kg BR/mol Ti.h.C$_{butadiene}$. Analysis of the microstructure showed 76% of 1,4-cis, 22% of 1,2-vinyl and 2% of 1,4-trans.

Example 4

The procedure of Example 1 was followed except that the CpTiF$_3$ was replaced with Cp*$_2$TiF. The activity was 6 kg BR/mol Ti.h.C$_{butadiene}$. Analysis of the microstructure showed 73% of 1,4-cis, 25% of 1,2-vinyl and 2% of 1,4-trans.

Example 5

The reactor was thoroughly heated, flushed several times with inert gas, thermo-statted and then charged with 1000 ml of hexane, 100 g of butadiene and 100 mmol of co-methylaluminoxane. A solution of CpTiF$_3$ in toluene (3×10$^{-5}$ mol/l) was injected into the reactor through a septum by means of a gastight syringe and the polymerization was started at a temperature of 70° C.

After a polymerization time of 150 minutes, the butadiene was discharged and the mixture was quenched with ethanol. Precipitation was induced by adding the toluene solution dropwise to ethanol containing Vulkanox KB as stabilizer, and the precipitate was filtered off and dried. The activity was 365 kg BR/mol Ti.h.C$_{butadiene}$. Analysis of the micro-structure showed 78% of 1,4-cis, 20% of 1,2-vinyl and 2% of 1,4-trans.

Example 6

The procedure of Example 1 was followed except that 49 ml of toluene were used and the butadiene was replaced with 50 ml of isoprene. The catalyst concentration was 5×10$^{-4}$ mol/l, the methylaluminoxane concentration was 0.15 mol/l and the polymerization time was 240 minutes. The activity was 840 g PI/mol Ti.h.C$_{isoprene}$.

Example 7

The procedure of Example 6 was followed except that the CpTiF$_3$ was replaced with MeCpTiF$_3$. The activity was 250 g PI/mol Ti.h.C$_{isoprene}$.

Example 8

The procedure of Example 6 was followed except that the CpTiF$_3$ was replaced with Cp*TiF$_3$. The activity was 29 g PI/mol Ti.h.C$_{isoprene}$.

Example 9

The procedure of Example 1 was followed except that the CpTiF$_3$ was replaced with CpTiCl$_3$. The activity was 45 kg BR/mol Ti.h.C$_{butadiene}$.

Example 10

The procedure of Example 1 was followed except that the CpTiF$_3$ was replaced with Cp*TiCl$_3$. The activity was 10 kg BR/mol Ti.h.C$_{butadiene}$.

Example 11

The procedure of Example 6 was followed except that the CpTiF$_3$ was replaced with CpTiCl$_3$. The activity was 28 g PI/mol Ti.h.C$_{isoprene}$.

Example 12

The procedure of Example 6 was followed except that the CpTiF$_3$ was replaced with Cp*TiCl$_3$. The activity was 8 g PI/mol Ti.h.C$_{isoprene}$.

Example 13

About 5 g of the metallocene of structure CpTiF$_3$, supported on an SiO$_2$/MAO precursor, were used in the polymerization, this amount containing approx. 0.15 mmol of the metallocene. The reaction was started at 60° C. in a vertical stirred glass autoclave, into which the polymerization-active material had previously been introduced under a nitrogen atmosphere, by applying a butadiene partial pressure of 2 bar. To improve the stirrability of the small amount of starting material, the catalyst can also be premixed or "extended", for example with a silica. The beginning of the reaction was signalled by a slight temperature rise (about 3° C.) inside the reactor and also by a visible increase in the total amount of stirred solid. After three hours the experiment was ended and the reaction product could be removed via the discharge cock at the bottom. The activity was 183 kg BR/mol Ti.h.

The gel content of the product was then determined, taking the heterogeneous support into account. The gel content was 0.8%.

Example 14

The procedure of Example 13 was followed except that the CpTiF$_3$ was replaced with CpTiCl$_3$. The activity was 37 kg BR/mol Ti.h. The gel content was 1.5%.

Example 15

Six rubber compounds with the compositions shown in Table 1 were prepared, said Table indicating the parts by weight of each component in the compounds. Compounds 3 and 6 are compounds according to the invention and compounds 1, 2, 4 and 5 are comparative compounds. Compounds 1–3 correspond to conventional tread compounds and compounds 4–6 correspond to conventional side wall compounds.

TABLE 1

| Rubber compound | C1 | C2 | C3 | C4 | C5 | C6 |
|---|---|---|---|---|---|---|
| Constituent | tread compound | | | side wall compound | | |
| NR(TSR 5 D. 700) | 80 | 80 | 80 | 60 | 60 | 60 |
| Buna ® CB 24 | 20 | | | 40 | | |
| Buna ® CB 10 | | 20 | | | 40 | |
| Metallocene BR | | | 20 | | | 40 |
| Carbon black N 375 | 55 | 55 | 55 | | | |
| Carbon black N 339 | | | | 55 | 55 | 55 |
| Renopal 450 | 3 | 3 | 3 | 6 | 6 | 6 |
| Stearic acid | 2.5 | 2.5 | 2.5 | 2 | 2 | 2 |
| Antilux ® 111 | 1 | 1 | 1 | 2 | 2 | 2 |
| Vulkanox ® 4010NA | 2.5 | 2.5 | 2.5 | 2.5 | 2.5 | 2.5 |
| Vulkanox ® HS/LG | 1.5 | 1.5 | 1.5 | 1.5 | 1.5 | 1.5 |
| ZnO active | 5 | 5 | 5 | 5 | 5 | 5 |
| Vulkacit ® NZ/EG | 1.2 | 1.2 | 1.2 | 0.8 | 0.8 | 0.8 |
| Rhenogran ® IS60-G | 1.56 | 1.56 | 1.56 | 2.2 | 2.2 | 2.2 |

NR is a commercially available natural rubber. The feedstock Buna® CB 24 is a commercial polybutadiene from BAYER AG which has been produced with a neodymium catalyst. The feedstock Buna® CB 10 is a commercial polybutadiene from BAYER AG which has been produced with a cobalt catalyst. Both polymers are characterized by a high cis content of more than 94%. Metallocene BR was produced according to the invention with the aid of the catalyst system comprising $CpTiCl_3$ and methylaluminoxane. The microstructure of this polymer is 74% of 1,4-cis, 2% of 1,4-trans and 20% of 1,2-vinyl. Carbon blacks N 375 and N 339 can be obtained e.g. from Cabot. The products Vulkanox® and Vulkacit® are from BAYER AG and the products Antilux® and Rhenogran® are from Rhein Chemie Rheinau GmbH.

Rubber compounds 1–6 were all prepared as follows: The constituents were introduced into a kneader at a temperature of 50° C. and a speed of rotation of 40 rpm and the compounds were then worked up on a roller.

The test pieces produced from the rubber compounds were used to determine the loss factor tan δ at 60° C. and a frequency of 10 Hz as specified in DIN 53513 and the resilience at 70° C. as specified in DIN 53512.

TABLE 2

| Rubber compound | | C1 | C2 | C3 | C4 | C5 | C6 |
|---|---|---|---|---|---|---|---|
| Resilience, 70° C. | [%] | 50 | 49 | 55 | 54 | 53 | 59 |
| tan δ, 60° C. | | 0.166 | 0.155 | 0.117 | 0.126 | 0.130 | 0.099 |

TABLE 3

| Example | Catalyst | |
|---|---|---|
| | | Activity [kg BR/mol Ti.h.$C_{butadiene}$] |
| 1 | $CpTiF_3$ | 54 |
| 9 | $CpTiCl_3$ | 45 |
| 2 | $MeCpTiF_3$ | 80 |
| 3 | $Cp*TiF_3$ | 40 |
| 10 | $Cp*TiCl_3$ | 10 |
| 4 | $Cp*_2TiF$ | 6 |
| 5 | $CpTiF_3$ | 365 |
| | | Activity [g PI/mol Ti.h.$C_{isoprene}$] |
| 6 | $CpTiF_3$ | 840 |
| 11 | $CpTiCl_3$ | 28 |
| 7 | $MeCpTiF_3$ | 250 |
| 8 | $Cp*TiF_3$ | 29 |
| 12 | $Cp*TiCl_3$ | 8 |

What is claimed is:

1. Catalyst system comprising the following formula:

$$R_nMX_m \quad (1),$$

wherein M is a metal, the radicals R are identical or different, can be in a bridged or unbridged form and are a mononuclear or polynuclear hydrocarbon radical coordinated with the central atom M, the radicals X are identical or different and are at least one fluorine atom and one hydrogen radical, $C_1$- to $C_{10}$-alkyl, $C_6$- to $C_{15}$-aryl, OR' or OC(O)R', R' being $C_1$- to $C_{10}$-alkyl, $C_6$- to $C_{15}$-aryl, alkylaryl, fluorine, fluoroalkyl or fluoroaryl each having 1 to 10 C atoms in the alkyl moiety and 6 to 20 C atoms in the aryl moiety, and n and m each denote the numbers 0, 1, 2, 3 or 4, wherein n+m<5, and optionally in combination with a co-catalyst, said catalyst system and said co-catalyst optionally, applied to an inorganic or organic support and is used in heterogeneous form.

2. Catalyst system according to claim 1, wherein M is titanium, zirconium and/or hafnium.

3. Catalyst system according to claim 1, wherein X is fluorine.

4. Catalyst system according to claim 1, wherein X is fluorine or a fluorine containing interhalogen.

5. Catalyst system according to claim 1. wherein R is preferably a substituted or unsubstituted cyclopentadienyl group $(R")_kCp$, R" being a hydrogen radical, $C_1$- to $C_{10}$-alkyl, $C_6$- to $C_{15}$-aryl, arylalkyl, alkenyl, fluoroalkyl or fluoroaryl and k being 1–5.

6. Catalyst system according to claim 1, wherein the catalyst component is selected from the group consisting of at least one of the following compounds: $CpTiF_3$, $MeCpTiF_3$, $Me_5CpTiF_3$, $(Me_5Cp)_2TiF$, $IndTiF_3$, $IndTiClF_2$, $IndTiCl_2F$, $MeIndTiF_3$, $MeIndTiClF_2$, $MeIndTiCl_2F$ and $Me_2IndTiF_3$.

7. Catalyst system according to claim 1, wherein alkylaluminoxanes, butyl-modified aluminoxanes, aluminum alkyls, fluorine-substituted triarylboranes or mixtures of the components are used as the co-catalyst.

8. Catalyst system according to claim 7, wherein methylaluminoxane and butyl-modified methylaluminoxane are used as the co-catalyst.

9. Catalyst system according to claim 1, wherein inert inorganic solids, silica gels, clays, aluminosilicates, talcum, zeolites, carbon black, inorganic oxides, silicon dioxide, aluminium oxide, magnesium oxide and titanium dioxide, and silicon carbide, preferably silica gels, zeolites and carbon black, and/or organic supports are used individually or in a mixture with one another as supports for the metal-organic compound of formula 1 and the co-catalyst.

10. A process for the production of diene rubbers by the polymerization of monomeric diene compounds with a catalyst system comprising the following formula:

$$R_nMX_m \quad (1),$$

wherein M is a metal, the radicals R are identical or different, can be in a bridged or unbridged form and are a mononuclear or polynuclear hydrocarbon radical coordinated with the central atom M, the radicals X are identical or different and are at least one fluorine atom and one hydrogen radical, $C_1$- to $C_{10}$-alkyl, $C_6$- to $C_{15}$-aryl, OR' or OC(O)R', R' being $C_1$- to $C_{10}$-alkyl, $C_6$- to $C_{15}$-aryl, alkylaryl, fluorine, fluoroalkyl or fluoroaryl each having 1 to 10 C atoms in the alkyl moiety and 6 to 20 C atoms in the aryl moiety, and n and m each denote the number 0, 1, 2, 3 or 4, wherein n+m<5, and optionally in combination with a co-catalyst, said catalyst system and said co-catalyst optionally, applied to an inorganic or organic support and is used in heterogeneous form, wherein said polymerization is carried out in solution, suspension or the vapor phase.

11. A diene rubber with cis contents of more than 50%, vinyl contents of 5–50% and gel contents of less than 5%, produced by the polymerization of monomeric diene compounds with a catalyst system comprising the following formula:

   (1), wherein M is a metal, the radicals R are identical or different, can be in a bridged or unbridged form and are a mononuclear or polynuclear hydrocarbon radical coordinated with the central atom M, the radicals X are identical or different and are at least one fluorine atom and one hydrogen radical, $C_1$- to $C_{10}$-alkyl, $C_6$- to $C_{15}$-aryl, OR' or OC(O)R', R' being $C_1$- to $C_{10}$-alkyl, $C_6$- to $C_{15}$-aryl, alkylaryl, fluorine, fluoroalkyl or fluoroaryl each having 1 to 10 C atoms in the alkyl moiety and 6 to 20 C atoms in the aryl moiety, and n and m each denote the number 0, 1, 2, 3 or 4, wherein n+m<5, and optionally in combination with a co-catalyst, said catalyst system and said co-catalyst optionally, applied to an inorganic or organic support and is used in heterogeneous form, wherein said polymerization is carried out in solution, suspension or the vapor phase.

12. A tire comprising diene rubbers with cis contents of more than 50%, vinyl contents of 5–50% and gel contents of less than 5%, produced by the polymerization of monomeric diene compounds with a catalyst system comprising the following formula:

   (1), wherein M is a metal, the radicals R are identical or different, can be in a bridged or unbridged form and are a mononuclear or polynuclear hydrocarbon radical coordinated with the central atom M, the radicals X are identical or different and are at least one fluorine atom and one hydrogen radical, $C_1$- to $C_{10}$-alkyl, $C_6$- to $C_{15}$-aryl, OR' or OC(O)R', R' being $C_1$- to $C_{10}$-alkyl, $C_6$- to $C_{15}$-aryl, alkylaryl, fluorine, fluoroalkyl or fluoroaryl each having 1 to 10 C atoms in the alkyl moiety and 6 to 20 C atoms in the aryl moiety, and n and m each denote the number 0, 1, 2, 3 or 4, wherein n+m<5, and optionally in combination with a co-catalyst, said catalyst system and said co-catalyst optionally, applied to an inorganic or organic support and is used in heterogeneous form, wherein said polymerization is carried out in solution, suspension or the vapor phase.

13. Industrial rubber goods comprising diene rubbers with cis contents of more than 50%, vinyl contents of 5–50% and gel contents of less than 5%, produced by the polymerization of monomeric diene compounds with a catalyst system comprising the following formula:

   (1), wherein M is a metal, the radicals R are identical or different, can be in a bridged or unbridged form and are a mononuclear or polynuclear hydrocarbon radical coordinated with the central atom M, the radicals X are identical or different and are at least one fluorine atom and one hydrogen radical, $C_1$- to $C_{10}$-alkyl, $C_6$- to $C_{15}$-aryl, OR' or OC(O)R', R' being $C_1$- to $C_{10}$-alkyl, $C_6$- to $C_{15}$-aryl, alkylaryl, fluorine, fluoroalkyl or fluoroaryl each having 1 to 10 C atoms in the alkyl moiety and 6 to 20 C atoms in the aryl moiety, and n and m each denote the number 0, 1, 2, 3 or 4, wherein n+m<5, and optionally in combination with a co-catalyst, said catalyst system and said co-catalyst optionally, applied to an inorganic or organic support and is used in heterogeneous form, wherein said polymerization is carried out in solution, suspension or the vapor phase.

14. A process for the modification of plastics comprising diene rubbers with cis contents of more than 50%, vinyl contents of 5–50% and gel contents of less than 5%, produced by the polymerization of monomeric diene compounds with a catalyst system comprising the following formula:

   (1), wherein M is a metal, the radicals R are identical or different, can be in a bridged or unbridged form and are a mononuclear or polynuclear hydrocarbon radical coordinated with the central atom M, the radicals X are identical or different and are at least one fluorine atom and one hydrogen radical, $C_1$- to $C_{10}$-alkyl, $C_6$- to $C_{15}$-aryl, OR' or OC(O)R', R' being $C_1$- to $C_{10}$-alkyl, $C_6$- to $C_{15}$-aryl, alkylaryl, fluorine, fluoroalkyl or fluoroaryl each having 1 to 10 C atoms in the alkyl moiety and 6 to 20 C atoms in the aryl moiety, and n and m each denote the number 0, 1, 2, 3 or 4, wherein n+m<5, and optionally in combination with a co-catalyst, said catalyst system and said co-catalyst optionally, applied to an inorganic or organic support and is used in heterogeneous form, wherein said polymerization is carried out in solution, suspension or the vapor phase.

15. Process according to claim 10, wherein the dienes used are butadiene, isoprene, pentadiene and 2,3-dimethylbutadiene, it being possible for said dienes to be used either individually or in a mixture with one another to form either homopolymers or copolymers of said dienes.

16. Process according claim 10, wherein the diene used in butadiene.

* * * * *